United States Patent [19]

Giller et al.

[11] 3,948,924

[45] Apr. 6, 1976

[54] CAROTENE STABILIZERS AND STABILIZATION OF CAROTENE

[76] Inventors: Solomon Aronovich Giller, ulitsa Pernavas, 10, kv. 76; Gunar Yanovich Dubur, ulitsa Suvorova, 117, kv. 12, both of Riga; Ian Rikhardovich Uldrikis, ulitsa Darza, 2, kv. 2, Elgava; Gunar Jamovich Tirzit, ulitsa Zhagatu, 22, kv. 33, Riga; Andrei Robertovich Valdman, ulitsa Lenina, 167, Riga; Ivan Markovich Zakharchenko, ulitsa P. Stuchki, 9/11, kv. 4, Riga; Yazep Yanovich Spruz, ulitsa Lenina, 103, kv. 8, Rezekne; Vitaly Evgenievich Ronis, ulitsa Ermolovoi, 17, kv. 66, Moscow; Alexandr Andrejevich Makarov, p/o Lugovaga, 3, Moskovskaya oblast, all of U.S.S.R.

[22] Filed: Feb. 26, 1974

[21] Appl. No.: 445,999

Related U.S. Application Data

[60] Continuation of Ser. No. 269,391, July 6, 1972, abandoned, which is a division of Ser. No. 55,288, July 15, 1970, abandoned.

[30] Foreign Application Priority Data

July 22, 1969 U.S.S.R............................. 1352174

[52] U.S. Cl........ 260/295.5 R; 260/297 R; 426/321
[51] Int. Cl.²........................................ C07D 211/80
[58] Field of Search.................. 260/295.5 R, 297 R

[56] References Cited
UNITED STATES PATENTS 2,075,359    3/1937    Salzberg et al.................. 260/290 R

OTHER PUBLICATIONS

Gustave Schnell et al., Chemical Abstracts, 70:28, 779c, 2/17/69.
Palecek et al., Chemical Abstracts 69:59, 104q 10/7/68.

*Primary Examiner*—Norman A. Drezin
*Attorney, Agent, or Firm*—Holman & Stern

[57] ABSTRACT

New stabilizers for carotene, which retard its oxidation and protect it against destruction, and which are 3,5-di-carbonyl derivatives of 2,6-dimethyl-1,4-dihydropyridine, conforming to the general formula

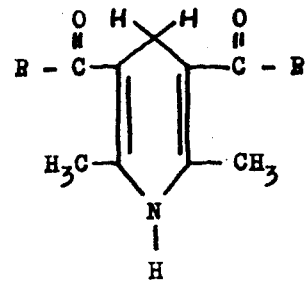

where R is a lower alkyl, such as methyl, or an alkoxy, such as an ethoxy group.

The introducing of said stabilizers into fodder products for animals such as, for instance, into grass four, makes it possible to preserve valuable nutritive properties of such products during a long period of time, of at least 6 months.

2 Claims, No Drawings

CAROTENE STABILIZERS AND STABILIZATION OF CAROTENE

This application is a continuation of copending application Ser. No. 265,391, filed July 6, 1972, now abandoned, which in turn is a divisional of application Ser. No. 55,288, filed July 15, 1970, now abandoned.

The present invention relates to antioxidants, and more particularly to carotene stabilizers.

The present invention has a particular reference to the stabilization of carotene in oil solutions, in fodder, and in any other carotene-containing products.

The problem of carotene preservation in fodder products under long-term storage conditions is of great importance for the national economy.

Carotene is known to be an important component of fodder products, being essential for the normal development of farm animals. However, easy oxidizability of carotene results in considerable losses thereof under storage conditions of fodder products. Therefore stabilization of carotene in such preparations as oil solutions, and stabilization of carotene in grass flour or in products containing grass flour, prove to be of great importance for further development of animal husbandry.

For preserving carotene in grass flour and in those fodder which comprise grass flour, a number of stabilizers have been proposed, ethoxychin (1,2-dihydro-6-ethoxy-2,2,4-trimethyl-quinoline,) being most widely used for this purpose.

Ethoxychin was proposed (cf. E. M. Bickoff, A. L. Livingston, J. Guggolz, C. R. Thompson, J. Agr. and Food Chem., 1954, 2, 1229) as a most effective fodder antioxidant for stabilizing carotene of alfalfa.

A method of stabilizing carotene in grass flour with ethoxychin introduced thereinto in the form of a solution is disclosed in M. S. TZhedek, Author's Certificate of the USSR No. 217270, 1967.

Said substance exhibits a good stabilizing effect, but proves to be somewhat toxic when administered per os to white mice. Moreover, it should be noted, that the process of producing ethoxychin is rather complicated and requires the use of vacuum distillation techniques. The production of ethoxychin is also associated with fire and explosion hazards. Ethoxychin is inconvenient in storage and handling, being a thick fluid, easily oxidizable, if stored in premises accessible to air.

The main object of the present invention is to provide a new stabilizer for preserving carotene in oil solutions, in fodder products, and in any other carotene-containing products, which stabilizer would be less toxic, more convenient for storage and transportation, while being not inferior to ethoxychin as to the effectiveness of carotene stabilization.

Said object is accomplished by using as carotene stabilizers 3,5-dicarbonyl derivatives of 2,6-dimethyl-1,4-dihydropyridines conforming to the general formula (I)

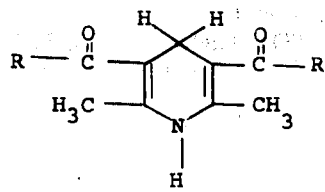

where R is a lower alkyl or an alkoxy.

The following compounds may be cited as separate representatives of the said group of carotene stabilizers:

2,6-dimethyl-3,5-diacetyl-1,4-dihydropyridine (II),
2,6-dimethyl-3,5-dicarboethoxy-1,4-dihydropyridine (III)

The stabilizing and antioxidant properties of the above-mentioned compounds become manifest, when they are studied for thermal autooxidation of an oil solution of carotene. The compounds conforming to the general formula (I) were mixed in various concentrations with an oil solution of carotene, and the mixture was subjected to thermal autooxidation at a temperature of 70°C over a period of 72 hours. For comparing the results obtained in experiments with the use of the compounds conforming to the general formula (I), similar experiments were carried out with the use of ethoxychin.

For stabilizing carotene in grass flour, the latter, after drying, was mixed with a solution of compounds conforming to the general formula (I), then packaged in sacks and kept in storage premises. The content of carotene in the stabilized grass flour was periodically assayed. In a similar fashion grass flour was treated with ethoxychin, and the results were compared.

The results thus obtained have shown, that the herein-proposed compounds conforming to the general formula (I) exhibit stabilizing and antioxidant properties with respect to carotene, that is, said compounds inhibit autooxidation of carotene. Due to this, carotene-containing products do not lose their nutritive properties during a period as long as 6 months, this being quite sufficient for winter storages.

Toxicological investigations of the above-said compounds conforming to the general formula (I) have shown them to be non-toxic. Thus, when carrying out comparative studies of the acute toxicity of ethoxychin and 2,6-dimethyl-3,5-dicarboethoxy-1,4-dihydropyridine, we have establihsed the $LD_{50}$ for ethoxychin, when administered per os to white mice, to be 2900 mg/kg, whereas for 2,6-dimethyl-3,5-dicarboethoxy-1,4-dihydropropyridine it exceeds 32000 mg/kg. Repeated daily administration per os of 2,6-dimethyl-3,5-dicarboethoxy-1,4-dihydropyridine to white rats in doses of 20 mg/kg during 6 months causes no toxic symptoms in the animals.

This is a sound proof of the fact that the herein-proposed compounds conforming to the general formula (I) are at least eleven times less toxic than ethoxychin.

When bacon pigs are fed with products containing grass flour stabilized with 2,6-dimethyl-3,5-dicarboethoxy-1,4-dihydropyridine, the accumulation of vitamin A in their liver increases from 7.7 to 15.6 mkg/g, i.e., twice as much.

It should also be pointed out, that the compounds conforming to the general formula (I) are advantageous in being produced by a simple and effective method, residing in reacting acyl acetone or acetoacetic ester with urotropin in the presence of ammonium acetate in an organic solvent, such as isopropanol. The compounds conforming to the general formula (I), produced by this method, are obtained in the form of crystalline substances, with a yield equal to 80–85% of the theoretical amount.

The compounds conforming to the general formula (I) are stable when stored in conventional packages, such as polyethylene sacks, and do not feature any caustic or desctructive properties.

Given hereinbelow are examples, illustrating the application of some of the compounds belonging to the said group. It should be pointed out, that the application of the compounds conforming to the general formula (I) as carotene stabilizers in fodder products is in no way limited to the examples that follow.

EXAMPLE 1

Solutions of catotene in sunflower oil were used, the concentration of carotene therein being 100 γ/ml. To 25 ml of said solution there were added 0.01 g of 2,6-dimethyl-3,5-dicarboethoxy-1,4-dihydropyridine (III), or 0.01 g of 2,6-dimethyl-3,5-diacetyl-1,4-dihydropyridine, or 0.01 g of ethoxychin. The resulting solutions were placed into a temperature-controlled cabinet and kept there over a period of 72 hours at a temperature of 70°C. The content of carotene in the samples was determined colorimetrically.

The obtained results are presented in Table 1.

Table 1

| Compounds tested | In oil solution | |
|---|---|---|
| | Quantity of compound, % | Residual quantity of carotene, in %, as against initial quantity (after 72 hrs) |
| Blank stock | — | 70 |
| Ethoxychin | 0.04 | 85 |
| Compound III | 0.04 | 86 |
| Compound II | 0.04 | 82 |

The obtained data indicate, that 3,5-dicarbonyl derivatives of 2,6-dimethyl-1,4-dihydropyridine feature practically the same antioxidant properties with respect to thermal autooxidation of carotene, as ethoxychin. The comparison of the carotene-stabilizing activity of 2,6-dimethyl-3,5dicarboethoxy-1,4-dihydropyridine (III) and 2,6-dimethyl-3,5-diacetyl-1,4-dihydropyridine (II) shows, that the activity of 2,6-dimethyl-3,5-dicarboethoxy-1,4-dihydropyridine is somewhat higher.

EXAMPLE 2

Grass flour was used, prepared from cultivated fodder grass by artificial drying thereof in high-temperature drivers. 500 kg of dry grass flour were treated in a mixer with 5 lit. of a 2% solution of 2,6-dimethyl-3,5-dicarboethoxy-1,4-dihydropyridine in a vegetable oil. After the mixing, the resulting stabilized grass flour was packaged in sacks and stored in a flat storage. The content of carotene in the samples was assayed once a month over a period of 6 months.

The variations observed in the content of carotene in the nonstabilized grass flour and in that stabilized with ethoxychin and with 2,6-dimethyl-3,5-dicarboethoxy-1,4-dihydropyridine (III) are illustrated in Table 2, for the storage conditions as specified hereinabove.

Table 2

| Storage time, days | Ambient temperature, °C | Relative humidity, % | Carotene content in grass flour, mg/kg | | | Increase in carotene preservation with the use of (%): | |
|---|---|---|---|---|---|---|---|
| | | | Non-stabilized | Stabilized with ethoxychin | Stabilized with compd. III | Ethoxychin | Compd. III |
| 0 | +8.0 | 86 | 169 | 153 | 154 | — | — |
| 30 | −7.5 | 90 | 137 | 151 | 153 | +17.6 | +18.3 |
| 60 | −3.5 | 90 | 129 | 149 | 151 | +21.1 | +21.8 |
| 90 | −18.1 | 62 | 118 | 150 | 150 | +28.1 | +27.6 |
| 120 | −2.5 | 75 | 106 | 140 | 145 | +28.8 | +31.5 |
| 150 | −6.7 | 64 | 97 | 131 | 134 | +28.2 | +28.6 |
| 180 | +10.3 | 75 | 83 | 115 | 120 | +26.1 | +28.8 |

As can be seen from the data presented in Table 2, the content of carotene in grass flour stabilized with 2,6-dimethyl-3,5-dicarboethoxy-1,4-dihydropyridine, after storage over a period of 6 months, proves to be 28.8% higher than in non-stabilized grass flour. Under similar conditions, ethoxychin enhances the preservation of carotene by 26.1%, this being 2,7% less than in case of using 2,6-dimethyl-3,5-dicarboethoxy-1,4-dihydropyridine.

What is claimed is:

1. A compound having the formula:

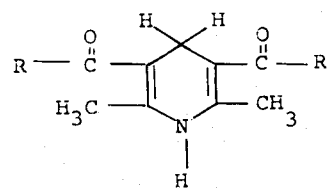

where R is lower alkyl.

2. 2,6-dimethyl-3,5-diacetyl-1,4-dihydropyridine.

* * * * *